United States Patent
Lee et al.

(10) Patent No.: US 10,503,772 B2
(45) Date of Patent: Dec. 10, 2019

(54) DEVICE AND METHOD FOR RECOMMENDING MULTIMEDIA FILE TO USER

(71) Applicant: HON HAI PRECISION INDUSTRY CO., LTD., New Taipei (TW)

(72) Inventors: Wen-Chia Lee, New Taipei (TW); Wei-Bin Liang, New Taipei (TW); Sheng-Feng Weng, New Taipei (TW); Chuan-Te Chan, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 311 days.

(21) Appl. No.: 15/482,934

(22) Filed: Apr. 10, 2017

(65) Prior Publication Data
US 2017/0300488 A1   Oct. 19, 2017

(30) Foreign Application Priority Data
Apr. 15, 2016   (TW) .............................. 105111951 A

(51) Int. Cl.
*G06F 7/00* (2006.01)
*G06F 16/435* (2019.01)
*A61B 5/16* (2006.01)
*G06F 16/44* (2019.01)

(52) U.S. Cl.
CPC ............ *G06F 16/436* (2019.01); *A61B 5/165* (2013.01); *G06F 16/44* (2019.01)

(58) Field of Classification Search
CPC ........ G06F 16/00; G06F 16/40; G06F 16/285; G06F 16/48; G06F 16/437
See application file for complete search history.

(56) References Cited

U.S. PATENT DOCUMENTS

| | | | | |
|---|---|---|---|---|
| 6,904,408 B1* | 6/2005 | McCarthy | ............ | A61B 5/6815 705/2 |
| 7,613,736 B2* | 11/2009 | Hicken | ................ | G11B 27/105 |
| 8,027,518 B2* | 9/2011 | Baker | ................ | G06K 9/00885 340/5.52 |
| 8,112,166 B2* | 2/2012 | Pavlovic | ................ | H03G 9/005 700/94 |
| 8,122,037 B2* | 2/2012 | McSheffrey | .......... | G06F 16/437 707/758 |
| 8,422,490 B2* | 4/2013 | Svendsen | ............... | G06Q 10/10 370/386 |

(Continued)

FOREIGN PATENT DOCUMENTS

TW   201112116 A1   4/2011
TW   201530326 A    8/2015

*Primary Examiner* — Daniel A Kuddus
(74) *Attorney, Agent, or Firm* — ScienBiziP, P.C.

(57) ABSTRACT

A multimedia file recommending device capable of matching entertainment file to user mood or state includes an input device to receive emotional value X sensed from or inputted by a user, a storage device, and a processor. The storage device stores multimedia files each associated with an emotional value. The processor selects a multimedia file from the multimedia database according to default rules, wherein a difference between the emotional value associated with the selected multimedia files and the emotional value X falling within a preset range. A multimedia file recommending method is also provided.

10 Claims, 4 Drawing Sheets

(56) References Cited

U.S. PATENT DOCUMENTS

| | | | | |
|---|---|---|---|---|
| 8,666,525 B2* | 3/2014 | Stefik | ............ | G06Q 30/02 |
| | | | | 700/94 |
| 8,732,180 B2* | 5/2014 | Lindahl | ............ | G11B 27/105 |
| | | | | 707/758 |
| 8,819,553 B2* | 8/2014 | Wood | ............ | G11B 27/034 |
| | | | | 715/716 |
| 9,292,179 B2* | 3/2016 | Svendsen | ............ | G06Q 10/10 |
| 2003/0154446 A1* | 8/2003 | Constant | ............ | H04L 51/38 |
| | | | | 715/256 |
| 2004/0021470 A1* | 2/2004 | Adams | ............ | G01R 31/086 |
| | | | | 324/522 |
| 2004/0225519 A1* | 11/2004 | Martin | ............ | G11B 27/002 |
| | | | | 705/53 |
| 2012/0157789 A1* | 6/2012 | Kangas | ............ | A61B 5/7228 |
| | | | | 600/300 |
| 2013/0297599 A1* | 11/2013 | Henshall | ............ | G11B 27/105 |
| | | | | 707/736 |
| 2014/0043224 A1* | 2/2014 | Lee | ............ | G06F 3/011 |
| | | | | 345/156 |
| 2014/0298364 A1* | 10/2014 | Stepanov | ............ | H04N 21/25 |
| | | | | 725/10 |
| 2015/0264431 A1* | 9/2015 | Cheng | ............ | H04N 21/44218 |
| | | | | 725/10 |
| 2017/0201779 A1* | 7/2017 | Publicover | ............ | H04W 4/21 |

* cited by examiner

DEVICE AND METHOD FOR RECOMMENDING MULTIMEDIA FILE TO USER

CROSS-REFERENCE TO RELATED APPLICATIONS

This application claims priority to Taiwan Patent Application No. 105111951 filed on Apr. 15, 2016.

FIELD

The subject matter herein generally relates to multimedia playing, and particularly to a device and method for recommending multimedia files to users.

BACKGROUND

Multimedia files are played on media players that can perceive multimedia types manually selected. Media players cannot recommend multimedia files automatically according to user's mood. A device and method for recommending multimedia files according to user's mood is provided.

BRIEF DESCRIPTION OF THE DRAWINGS

Implementations of the present technology will now be described, by way of example only, with reference to the attached figures.

DETAILED DESCRIPTION

Figure 1:
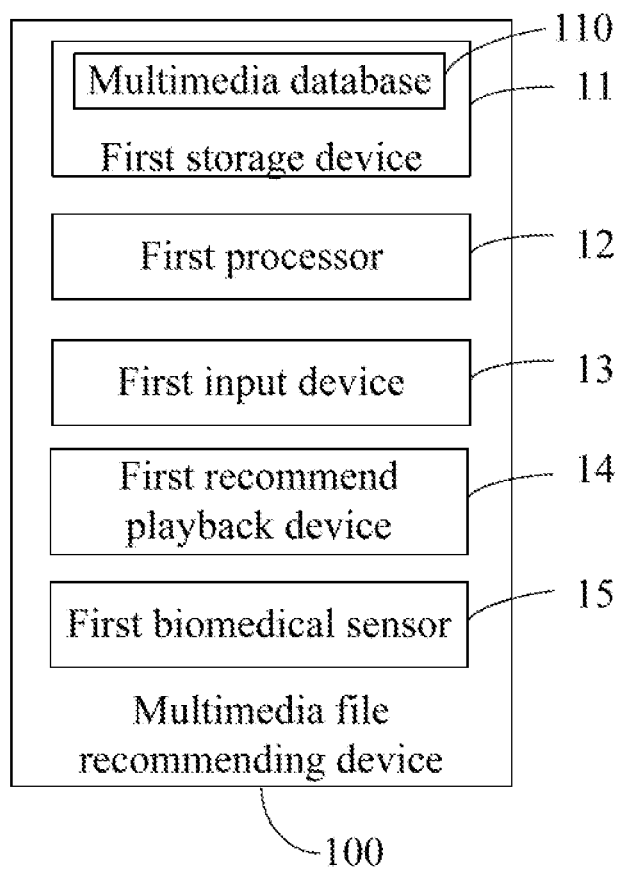
FIG. 1 is a block diagram illustrating a first embodiment of a multimedia file recommending device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

The term "comprising" means "including, but not necessarily limited to", it specifically indicates open-ended inclusion or membership in a so-described combination, group, series, and the like.

FIG. 1 illustrates a first embodiment of a multimedia file recommending device 100 (hereinafter "recommending device 100"). The recommending device 100 can recommend multimedia files for users according to mood of the users. In the first exemplary embodiment, the recommending device 100 at least includes a first storage device 11, a first processor 12, a first input device 13, a first recommend playback device 14, and a first biomedical sensor 15. In the first exemplary embodiment, the first storage device 11 can be, but is not limited to, an internal storage system, such as a flash memory, a random access memory (RAM) for temporary storage of information, and/or a read-only memory (ROM) for permanent storage of information. The first storage device 11 can also be a storage system, such as a hard disk, a storage card, or a data storage medium. In the first exemplary embodiment, the first processor 12 can be, but is not limited to, a central processing unit, a digital signal processor, or a single chip, for example. In the first exemplary embodiment, the recommending device 100 can be, but is not limited, a smart phone, a tablet, and the like.

The first storage device 11 stores a multimedia database 110. The multimedia database 110 stores a number of emotional values, each emotional value corresponds to one multimedia file. The multimedia files can be music, movies, and the like. In the first exemplary embodiment, the multimedia files are stored in first storage device 11. In other embodiment, the multimedia files further can be stored in other devices, which communicate with the commending device 100. For example, the multimedia files can be stored in a server that communicates with the recommending device 100.

The emotional value is configured to indicate the mood of a user. In the first exemplary embodiment, the multimedia music files are taken as an example. The method enables the first processor 12 to acquire sound characteristics of each of the music files, determine a model parameter corresponding to each sound characteristic by using a known statistical method, and calculate the emotional value of each music file.

The first input device 13 is configured for receiving users' input. For example, users can input the emotional values and select a favorite music type and/or file by the input device. In the exemplary embodiment, the first input device 13 can be, but is not limited to, a touch screen, a keyboard, or a voice-input device such as microphone.

The first biomedical sensor 15 is configured to detect physiological data of the user, such as heart rate, blood pressure, respiratory rate, and/or skin temperature. In the first exemplary embodiment, the first biomedical sensor 15 can be built within the recommending device 100. The biomedical sensor 15 can be a pressure sensor or a temperature sensor, and the recommending device 100 can be a wearable device, such as a smart watch or a smart wristband. Such wearable device has function of detecting physiological data and a function of activating playback of multimedia files. In other embodiments, the first biomedical sensor 15 can be located externally relative to the recommending device 100 and can communicate with the recommending device 100 wirelessly or by wires. The first biomedical sensor 15 can be a wearable device, such as smart watch or smart wristband. The recommending device 100 can be an portable electronic device having a function of playing back multimedia files, such as a mobile phone, a tablet computer, and the like.

Figure 2:
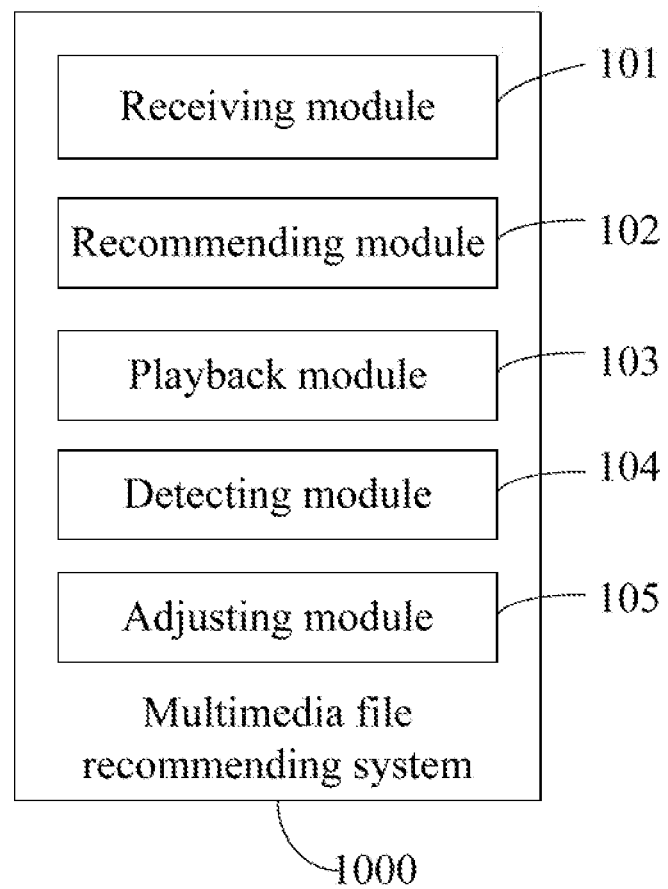
FIG. 2 is a block diagram illustrating a first embodiment of a multimedia file recommending system operating in the device of FIG. 1.

In the first exemplary embodiment, the first storage device 11 further can store a multimedia file recommending system 1000 (hereinafter "recommending system 1000"). The recommending system 1000 can include a number of modules, which are collection of software instructions stored in the first storage device 11 and executed by the first processor 12. Referring to FIG. 2, in at least one embodiment, the recommending system 1000 can include a receiving module 101, a recommending module 102, a playback module 103, a detecting module 104, and an adjusting module 105.

The receiving module 101 receives an emotional value X inputted by the user through the first input device 13.

The recommending module 102 selects a multimedia file from the multimedia database 110 according to a default rule or rules. A default rule may be that a difference between the emotional value associated with the selected multimedia files and the emotional value X inputted by the user falls within a preset range.

In the first embodiment, the default rule can include selecting one or more music files, and a difference is between the emotional value of the one or more selected multimedia files and an inputted emotional value falls within a preset range. One multimedia file may be selected from all the selected multimedia files randomly.

In another embodiment, the default rule can include selecting one or more multimedia files, wherein a difference between the emotional values associated with the selected music files and the inputted emotional value falls within a preset range. The one multimedia file, which is played least frequently, is then selected. In this embodiment, the database 110 further stores the number of times each multimedia file has been played.

In another embodiment, the default rule can include selecting one or more multimedia files, in which a difference is between the emotional values of the one or more selected multimedia files and the inputted emotional value falls within a preset range, deleting one or more selected multimedia files that the user dislike, and selecting one multimedia file from the remaining selected multimedia files randomly.

In another embodiment, the default rule can include selecting one multimedia file, which has an associated emotional value closest to the inputted emotional value.

The playback module 103 acquires the multimedia file selected by the recommending module 102 and plays back the acquired multimedia file by using the recommend playback device 14.

The detecting module 104 can detect the physiological data of the user by using the first biomedical sensor 15 when the user plays back the multimedia file for a preset time period. For example, the preset time period can be two minutes of the multimedia file playback or one half of the multimedia file being played back.

The adjusting module 105 acquires the physiological data from the detecting module 104, and calculates a current emotional value Z of the user according to the physiological data of the user and a predetermined process. In the first embodiment, the predetermined process can be an Arousal-Valence algorithm. The predetermined process can be other algorithm, and not limited by the example provided herein.

The adjusting module 105 selects another multimedia file according to the current emotional value Z of the user and the emotional value X inputted by the user. The adjusting module 105 calculates a compensation value Y according to the formula Y=X−Z, and then the adjusting module 105 selects a multimedia file that has an associated emotional value closest to X+Y.

The playback module 103 acquires the multimedia file selected by the adjusting module 105 and plays back the multimedia file by the first recommend playback device 14.

Figure 3:
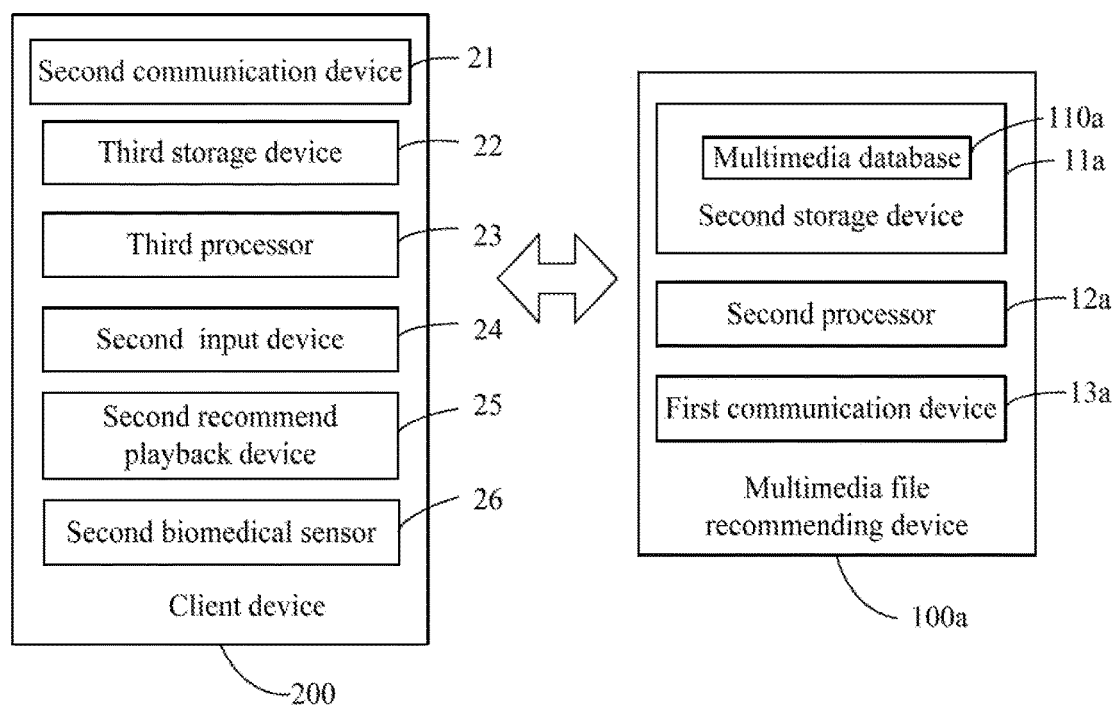
FIG. 3 is a block diagram illustrating a second embodiment of a multimedia file recommending device.

FIG. 3 illustrates a second embodiment of a multimedia file recommending device 100a (hereinafter "recommending device 100a"). In the second exemplary embodiment, the recommending device 100a can include a second storage device 11a, a second processor 12a, and a first communication device 13a. In the second embodiment, the recommending device 100a can be a server. The recommending device 100a communicates with at least one client device 200 via the first communication device 13a. Each client device 200 can include, but is not limited to, a second communication device 21 for communicating with the first communication device 13a, a third storage device 22, a third processor 23, a second input device 24, a second recommend playback device 25, and a second biomedical sensor 26. A database 110a is stored in the second storage 11a. The database 110a stores a number of emotional values, each emotional value corresponds to or is associated with one multimedia file.

The client device 200 receives an emotional value X input by the user via the second input device 24, and sends the emotional value X to the recommending device 100a via the second communication device 21. When the recommending device 100a receives the emotional value X, the recommending device 100a selects a multimedia file from the database 110a according to the default rule. Herein, the default rule is a difference between the emotional value of the selected multimedia files and the emotional value X inputted by the user falling in a preset range. The recommending device 100a sends the selected multimedia file to the client device 200. When the client device 200 receives the selected multimedia file from the recommending device 100a, the second recommend playback device 25 acquires the selected multimedia file for playback. The client device 200 further detects physiological data of the user by using the second biomedical sensor 26 when the user is listening to/watching the multimedia file, and sends the physiological data to the recommending device 100a. The recommending device 100a calculates a current emotional value Z of the user according to the physiological data of the user and a predetermined process. In this embodiment, the predetermined process can be an Arousal-Valence algorithm. The recommending device 100 sends the selected multimedia file to the client device 200.

Figure 4:
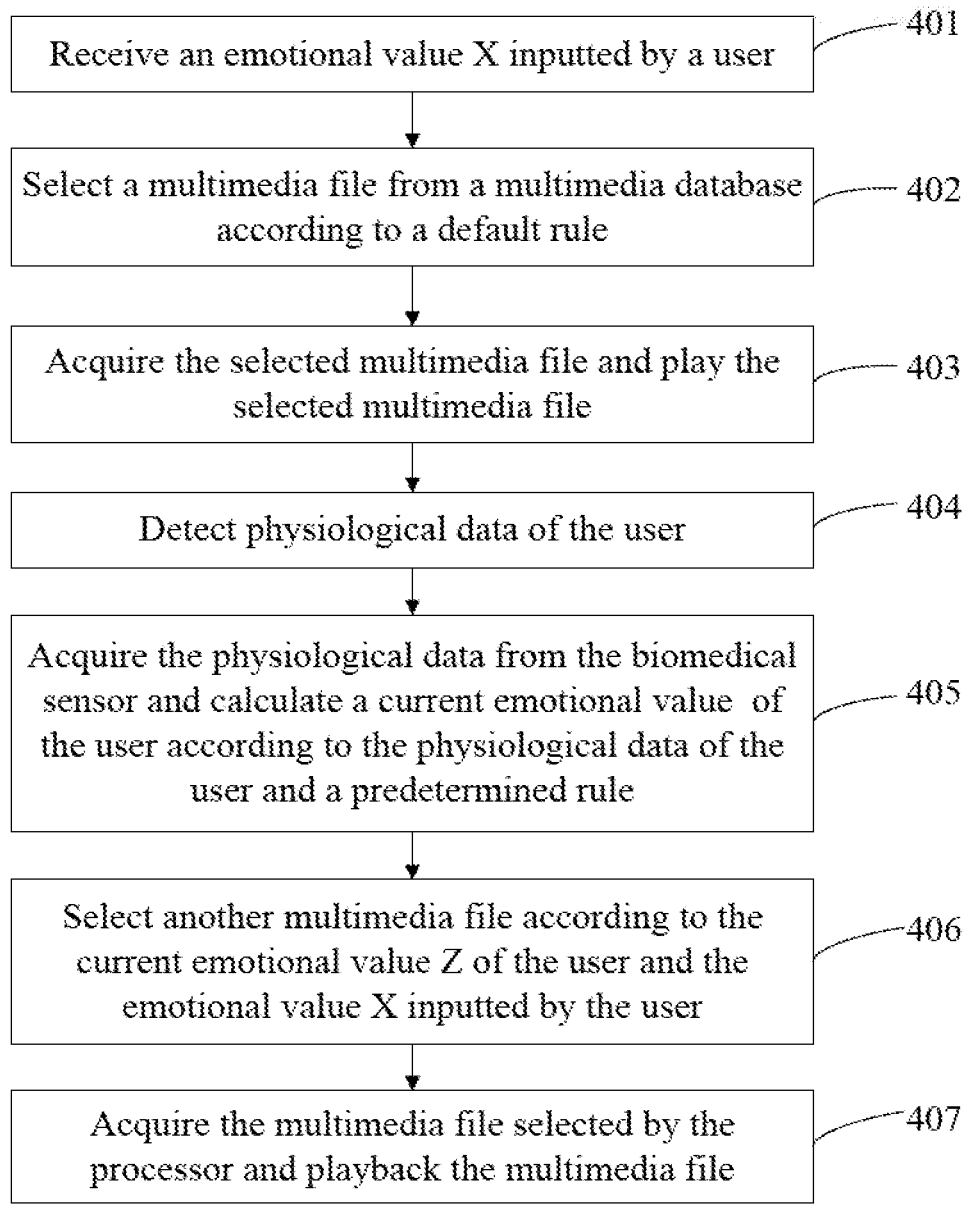
FIG. 4 is a flowchart illustrating an embodiment of a multimedia file recommending method.

FIG. 4 illustrates a multimedia file recommending method applied in a multimedia file recommending device. The method is provided by way of example, as there are a variety of ways to carry out the method. The method described below can be carried out using the configurations illustrated in FIG. 1, for example, and various elements of these figures are referenced in explaining the example method. Each block shown in FIG. 4 represents one or more processes, methods, or subroutines carried out in the example method. Additionally, the illustrated order of blocks is by example only and the order of the blocks can be changed. The example method can begin at block 401.

At block 401, a processor receives an emotional value X inputted by a user through an input device. In one embodiment, the input device can be located within the multimedia file recommending device. In other embodiments, the input device can be located in the client device, which communicates with the multimedia file recommending device.

At block 402, the processor selects a multimedia file from a multimedia database according to a default rule or rules. The default rule may be that a difference between the emotional value associated with the selected multimedia files and the emotional value X inputted by the user falls within a preset range.

In the first embodiment, the default rule can include selecting one or more music files, wherein a difference between the emotional values associated with the selected multimedia files and an inputted emotional value falls within a preset range. One multimedia file may be selected from all the selected multimedia files randomly.

In another embodiment, the default rule can include selecting one or more multimedia files, wherein a difference between the emotional values associated with the selected multimedia files and the inputted emotional value falls within a preset range. The one multimedia file, which is played least frequently, is then selected. In this embodiment, the database 110 further stores the number of times each multimedia file has been played.

In another embodiment, the default rule can include selecting one or more multimedia files, wherein a difference between the emotional values of the selected multimedia files and the inputted emotional value falls within a preset range, deleting one or more selected multimedia files that the user dislike, and selecting one multimedia file from the remaining of the selected multimedia files randomly.

In another embodiment, the default rule can include selecting one multimedia file, which has an associated emotional value closest to the inputted emotional value.

At block 403, a recommend playback device acquires the selected multimedia file and plays back the selected multimedia file. In one embodiment, the recommend playback device can be located within the multimedia file recommending device. In other embodiments, the recommend playback device can be located within a client device, which communicates with the multimedia file recommending device, and at block 403, the multimedia file recommending device sends the selected multimedia file to the client device.

At block 404, a biomedical sensor detects the physiological data of the user when the user plays back the multimedia file played by the recommend playback device for a preset time period. For example, the preset time period can be two minutes of the multimedia file playback or one half of the multimedia file being played. In one embodiment, the biomedical sensor can be located within the multimedia file recommending device. In other embodiments, the biomedical sensor can be located in the client device, which communicates with the multimedia file recommending device.

At block 405, the processor acquires the physiological data from the biomedical sensor, and calculates a current emotional value Z of the user according to the physiological data of the user and a predetermined process. In the first embodiment, the predetermined process can be an Arousal-Valence algorithm.

At block 406, the processor selects another multimedia file according to the current emotional value Z of the user and the emotional value X inputted by the user. The processor calculates a compensation value Y according to the formula Y=X−Z, and then selects a multimedia file that has an associated emotional value closest to X+Y.

At block 407, the recommend playback device acquires the multimedia file selected by the processor and plays back the multimedia file.

It is believed that the present embodiments and their advantages will be understood from the foregoing description, and it will be apparent that various changes may be made thereto without departing from the spirit and scope of the disclosure or sacrificing all of its material advantages, the examples hereinbefore described merely being exemplary embodiments of the present disclosure.

What is claimed is:

1. A multimedia file recommending device comprising:
   an input device to receive an emotional value X inputted by a user;
   a storage device to store a multimedia database, wherein the multimedia database stores a plurality of emotional values, each emotional value corresponds to one multimedia file; and
   a processor to select a multimedia file according to a default rule, wherein the default rule is a difference between the emotional value associated with the selected multimedia files and the emotional value X inputted by the user falling within a preset range;
   a biomedical sensor to detect physiological data of the user when the user plays back the multimedia file for a preset time period;
   wherein the processor acquires the physiological data from the biomedical sensor, calculates a current emotional value Z of the user according to the physiological data of the user and a predetermined process, and selects another multimedia file according to the current emotional value Z of the user and the emotional value X inputted by the user, wherein the processor calculates a compensation value Y according to the formula Y=X−Z, and selects the multimedia file having an emotional value closest to X+Y.

2. The multimedia file recommending device of claim 1, wherein the default rule comprises: selecting one or more music files, wherein a difference between the emotional values associated with the selected multimedia files and the inputted emotional value X falling within a preset range, and selecting one multimedia file from all the selected multimedia files randomly.

3. The multimedia file recommending device of claim 1, wherein the default rule comprises: selecting one or more music files, wherein a difference between the emotional values associated with the selected music files and the inputted emotional value X falling within a preset range, and selecting one multimedia file played least frequently.

4. The multimedia file recommending device of claim 1, wherein the default rule comprises: selecting one or more multimedia files, wherein a difference between the emotional value of the selected multimedia files and the inputted emotional value X falling within a preset range; deleting one or more selected multimedia files; and selecting one multimedia file from the remaining selected multimedia files randomly.

5. The multimedia file recommending device of claim 1, further comprising a communication device to communicate with at least one client device and at least one multimedia database, wherein the multimedia database stores a plurality of emotional values, each emotional value corresponds to one multimedia file; the processor further receives the emotional value X inputted by the user from the client device and sends the selected multimedia files to the client device.

6. A multimedia file recommending method applied in a multimedia file recommending device, the multimedia file recommending device comprising a processor and a storage device to store a multimedia database, the multimedia database stores a plurality of emotional values, each emotional value corresponds to one multimedia file, the method comprising:
   receiving an emotional value X inputted by a user by the processor; and
   the processor selecting a multimedia file from the multimedia database according to a default rule, wherein the default rule is a difference between the emotional value associated with the selected multimedia files and the emotional value X inputted by the user falling within a preset range;

detecting physiological data of the user by using a biomedical sensor when the user plays back the multimedia file for a preset time period; and calculating a current emotional value Z of the user according to the physiological data of the user and a predetermined rule, and selecting another multimedia file according to the current emotional value Z of the user and the emotional value X inputted by the user, wherein the predetermined rule comprises the processor calculating a compensation value Y according to the formula Y=X−Z, and selecting the multimedia file having an emotional value closest to X+Y.

7. The multimedia file recommending method of claim 6, wherein the default rule comprises: selecting one or more music files, wherein a difference between the emotional values associated with the selected multimedia files and the inputted emotional value X falling within a preset range, and then selecting one multimedia file from all the selected multimedia files randomly.

8. The multimedia file recommending method of claim 6, wherein the default rule comprises: selecting one or more music files, wherein a difference between the emotional values associated with the selected music files and the inputted emotional value X falling within a preset range, and selecting one multimedia file played least frequently.

9. The multimedia file recommending method of claim 6, wherein the default rule comprises: selecting one or more multimedia files, wherein a difference between the emotional value of the selected multimedia files and the inputted emotional value X falling within a preset range; deleting one or more selected multimedia files; and selecting one multimedia file from the remaining of the selected multimedia files randomly.

10. A multimedia file recommending method applied in a client device communicating with a multimedia file recommending device, the multimedia file recommending device communicating with a multimedia database, the multimedia database storing a plurality of emotional values, each emotional value corresponds to one multimedia file, the client device comprising a communication device, an input device, a biomedical sensor, and a recommend playback device, the method comprising;

receiving an emotional value X inputted by a user by the input device of the client device;

sending the emotional value X to the multimedia file recommending device the communication device;

receiving a multimedia file selected from the multimedia database according to a default rule by the communication device, from the multimedia file recommending device; and playing back the multimedia file by the recommend playback device of the client;

detecting physiological data of the user by using the biomedical sensor when the user plays back the multimedia file for a preset time period; and sending the physiological data to the multimedia file recommending device and receiving another multimedia file selected from the multimedia database having an emotional value closest to X+Y, wherein Y is calculated according to a formula Y=X−Z, wherein Z is a current emotional value of the user calculated according to the physiological data of the user and a predetermined rule.

* * * * *